United States Patent [19]

Appleton et al.

[11] Patent Number: 5,698,695
[45] Date of Patent: Dec. 16, 1997

[54] PROCESS FOR PREPARING 2-AMINO-4,6-DICHLOROPYRIMIDINE

[75] Inventors: Wayne Craig Appleton, Charleston, W. Va.; Patti Ann Parziale, Wilmington, Del.

[73] Assignee: E. I. Du Pont de Nemours and Company, Wilmington, Del.

[21] Appl. No.: 596,362

[22] PCT Filed: Jul. 26, 1994

[86] PCT No.: PCT/US94/08206

§ 371 Date: Mar. 5, 1996

§ 102(e) Date: Mar. 5, 1996

[87] PCT Pub. No.: WO95/07265

PCT Pub. Date: Mar. 16, 1995

Related U.S. Application Data

[63] Continuation-in-part of Ser. No. 119,777, Sep. 10, 1993, abandoned.

[51] Int. Cl.$^6$ .................. C07D 239/30; C07D 239/42
[52] U.S. Cl. ................................................. 544/330
[58] Field of Search ................................. 544/330

[56] References Cited

U.S. PATENT DOCUMENTS

| | | | |
|---|---|---|---|
| 3,991,190 | 11/1976 | Garzia et al. | 424/251 |
| 4,929,729 | 5/1990 | Haga et al. | 544/330 |

FOREIGN PATENT DOCUMENTS

| | | |
|---|---|---|
| 0 329 170 | 8/1989 | European Pat. Off. . |
| 0 372 934 | 6/1990 | European Pat. Off. . |
| 2 269 346 | 11/1975 | France . |

OTHER PUBLICATIONS

Banks et al., *J. Am. Chem. Soc.* 73:3011–3012 (1951).
M. Israel et al., *J. Med. Chem.*, 7:792–799 (Nov. 1964).

*Primary Examiner*—John M. Ford

[57] ABSTRACT

A process comprising reacting 2-amino-4,6-dihydroxypyrimidine or its salt with phosphorus oxychloride without the use of a solvent or excessive quantities of phosphorus oxychloride.

5 Claims, No Drawings

PROCESS FOR PREPARING 2-AMINO-4,6-DICHLOROPYRIMIDINE

CROSS-REFERENCE TO RELATED APPLICATIONS

This application is a 371 of PCT/US94/08206 filed Jul. 26, 1994, published as WO95/07265 Mar. 16, 1995, which is a continuation-in-part of U.S. application Ser. No. 08/119,777 filed Sep. 10, 1993, now abandoned.

BACKGROUND

The present invention is an improved process for producing 2-amino-4,6-dichloropyrimidine. Said pyrimidine is useful as an intermediate in the production of pesticides and pharmaceuticals.

U.S. Pat. No. 3,991,190 and Banks et at., J. Am. Chem. Soc., (1951), 73, 3011–3012 disclose processes for making the subject pyrimidine wherein 2-amino-4,6-dihydroxypyrimidine and excess phosphorus oxychloride (used as both a reactant and solvent) are reacted under reflux (105°–110° C.) in the presence of dimethylaniline (hereinafter referred to as "neat" processes). U.S. Pat. No. 4,929,729 and Kokai Patent No. Sho 64(1989)-83071 disclose processes for making the subject pyrimidine wherein 2-amino-4,6-dihydroxypyrimidine and phosphorus oxychloride are reacted in inert solvent at reflux in the presence of acid-removing agent (hereinafter referred to as "solvent" processes).

The present invention is advantageous over the prior methods for one or more of the following reasons: i) improved product yield, ii) shorter reaction time, iii) reduced amounts of phosphorus oxychloride which is a highly corrosive and toxic reagent and iv) no need for recycle or disposal of inert solvent.

SUMMARY OF THE INVENTION

This invention is an improved process for the preparation of 2-amino-4,6-dichloropyrimidine (I) comprising reacting 2-amino-4,6-dihydroxypyrimidine (I) and phosphorus oxychloride (III) according to Equation 1:

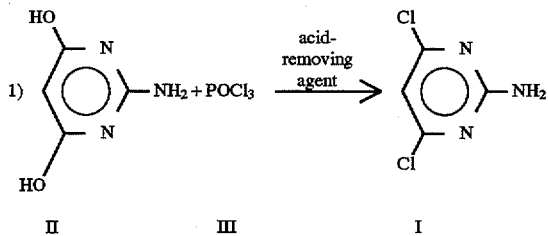

the reaction being conducted by charging an acid-removing agent such as an amine base, most preferably N,N-dimethylaniline, to a mixture of II and III at a temperature of from 40° to 90° C., preferably 40° to 80° C., most preferably 55°–68° C.; the mole ratio of (III) to (II) being from about 2.8:1 to 5:1, preferably about from 3.4:1 to 4.2:1, and the mole ratio of acid-removing agent to II being from about 1.7–2.5:1. The process is carried out without the need for reflux temperatures, large excesses of phosphorus oxychloride or inert solvent.

DETAILS OF THE INVENTION

In accordance with present invention, the process is typically carried out by first slurrying 2-amino-4,6-dihydroxypyrimidine (II) in phosphorus oxychloride (III) in the ratio of one mole of II in 2.8 to 5 mole, preferably 3.4 to 4.2 mole, of III. Starting materials II and III are known and commercially available (Aldrich Chemical Co., Milwaukee, Wis.). The ratio of III to II is determined by the minimum amount of III needed to provide a slurry with low enough viscosity to be pumped and processed readily. More than 5:1 moles of III to II is not desirable and is just lost in the quench step, described hereinafter.

The slurry of II and III is heated to reaction temperature which can be from 40° to 90° C. For reasons of economy and purity of final product, the reaction temperature is preferably 40°–80° C., and most preferably 55°–68° C. At temperatures above 90° C., the yield decreases due relatively increased side reaction. At temperatures below 40° C., the reaction time becomes unacceptably slow.

At reaction temperature, acid-removing agent is charged, either continuously or in small increments, to the slurry of II and III. The total amount charged is preferably 1.7 to 2.5 mole of acid-removing agent per mole of II in the slurry. Reaction during this step is rapid and exothermic, and the rate of addition of acid-removing agent is limited by the ability to maintain the proper reaction temperature range. Amine bases which can be employed as acid-removing agents include N,N-dimethylaniline, N,N-diethylaniline, triethylamine, pyridine and picoline. Most preferred is N,N-dimethylaniline.

A hold period at reaction temperature at the end of addition of the acid-removing agent can be employed to make certain II is completely reacted, although this step is not required.

The product pyrimidine (I) can be isolated by quenching the reaction mixture with water to consume the small excess of phosphorous oxychloride; then filtering, washing and drying the product crystals by standard methods. Product degradation can occur in the quench step, the risk of degradation increasing as a function of increasing temperature and acidity. The temperature in the quench reaction can increase due to the exothermic reaction of water with excess phosphorus oxychloride, and cooling may be required to maintain a temperature preferably less than about 60° C. Also, the acidity of the quench mixture increases due to the generation of hydrochloric and phosphoric acids during the reaction. It is advantageous to limit the amount of excess III in the reaction mixture to the lowest level possible so that the heat and acid build-up in the quench step is kept to a minimum. The amount of quench water used is preferably about 4 volumes of water to volume of III charged to the original reaction mixture. Using high amounts of water creates an necessary increase in processing time and excessive aqueous waste; too little water causes temperature control problems and increased pH. The product is preferably filtered as soon as possible after the quench is complete, Alternatively, the product can be isolated without a water quench by simply filtering the reaction mixture and washing and drying the product by standard methods. The product yield is typically lower without the water quench; however, some of that yield loss can be recovered by recycling the filtrate to subsequent runs.

One skilled in the art will appreciate that the process of the present invention can be carried out as a batch or continuous operation.

The process of the present invention is advantageous over the neat processes of the prior art in that improved product yields are obtained with shorter reaction times. A key aspect of the present invention is the discovery that controlled addition of acid-removing agent to the reaction mixture of II and III permits lower reaction temperatures and higher product yield. Also, it was discovered that a large excess of III is not necessary and that levels of III can be reduced to the point where recovery of the excess can be economically avoided. A comparison of the present process versus other processes employing no inert solvent is presented in Table 1.

The present invention is also advantageous over prior art processes employing inert solvent. As cited in U.S. Pat. No. 4,929,729, the inert solvent processes are advantageous over the prior art neat processes known at that time because 1) use of inert solvent decreases the amount of difficult-to-handle III needed in the reaction thereby reducing handling problems and simplifying or eliminating entirely recovery of III, and 2) by using solvent it is possible to control of the chlorination temperature to provide more optimum reaction conditions so that higher product yield is obtained. Now, according to the present invention, the benefits of the inert solvent processes are achieved without the use of solvent thereby eliminating the problems of recycling and/or disposing of organic solvent. By careful addition of acid-removing agent to the reaction mixture, temperature can be controlled in the absence of inert solvent and high product yield is still obtained. Also, substantially reduced amounts of III can be used, relative to the neat processes, without compensating therefor with inert solvent.

This mixture was then heated to 55°–60° C. N,N-dimethylaniline (229.4 g, 2.10 mole) was added over 3 h while maintaining the reaction temperature between 60°–70° C. After the addition, the reaction mixture was stirred for an additional 1 hour. To a second reaction vessel containing 1.08 L of water and equipped with a cooling jacket and a stirrer is pumped the reaction mixture from the first reactor. The rate of transfer was adjusted such that the temperature of the second reaction vessel was kept below 60° C. This quench is exothermic and produces hydrochloric and phosphoric acid. The resulting aqueous slurry was cooled to below 35° C. and filtered and washed with water. The collected crystals were air dried to yield 145.7 g (86% yield, 99.2% assay) of the title product containing no detectable starting material.

COMPARATIVE EXAMPLE A

Preparation of 2-Amino-4,6-Dichloropyrimidine Following the Procedure of Banks et al.

In a 4-neck 250 mL round-bottom flask equipped with stirrer, heating mantle and condenser was charged with 112.5 mL (1.22 moles) of phosphorous oxychloride, 19.06 g (0.15 mole) of 2-amino-4,6-dihydroxypyrimidine and 0.75 mL (2.10 mole) of N,N-dimethylaniline. The reaction mixture was heated to reflux for 8 h. The excess phosphorus

TABLE 1

Comparison of Chlorination Procedures of 2-amino-4,6-dihydroxypyrimidine with Phosphorus Oxychloride and N,N-dimethylaniline in the absence of a solvent[a]

| EXAMPLE | Molar Ratio $POCl_3/II$ | Molar Ratio $DMA/II$[b] | Reaction time (hours) | Reaction temp. (°C.) | Yield (%) |
|---|---|---|---|---|---|
| EXAMPLE 1 of present invention[c] | 3.52 | 2.02 | 4 | 60 | 86[d] |
| COMPARATIVE EXAMPLE A of present invention[f] | 8.05 | 0.039 | 8 | 107 | 55 |
| Comparative Example B (taken from Banks et al., J. Am. Chem. Soc., (1951), 73, 3011–3012, Experimental I) | 8.05 | 0.039 | 8 | 107 | >80 |
| Comparative Example C (taken from U.S. Pat. No. 3,991,190, Example 1) | 9 | 3 | 8 | 107 | 70[e] |
| Comparative Example D (taken from Kokai Patent No. Sho 64(1989)-83071, Comparative Example 1[g]) | 8.05 | 0.039 | 8 | 107 | 45.5 |

[a]Does not include the procedure reported by Israel, et al., J. Med. Chem., (1964), 7, 792 wherein a 50% (purified) yield was obtained as no experimental details were provided.
[b]DMA = N,N-dimethylaniline.
[c]Conducted in accordance with the process of the present invention.
[d]99.2% assay.
[e]crystallized from benzene.
[f]Conducted in accordance with J. Am. Chem. Soc., (1951), 73, 3011–3012 using 19.06 g of 2-amino-4,6-dihydroxypyrimidine and 187.06 g of $POCl_3$.
[g]Conducted in accordance with J. Am. Chem. Soc., (1951), 73, 3011–3012 using 1 g of 2-amino-4,6-dihydroxypyrimidine and 9.7 g of $POCl_3$.

EXAMPLE 1

Preparation of 2-Amino-4,6-Dichloropyrimidine By the Present Method

In a 4-neck 1000 mL round-bottom flask equipped with stirrer, heating mantle, condenser and an addition funnel was charged 556.8 g (3.63 mole) of phosphorus oxychloride and 131.2 g (1.03 moles) of 2-amino-4,6-dihydroxypyrimidine.

oxychloride was removed under reduced pressure by distillation. When the pot temperature reached 100° C., the distillation was terminated. After cooling to more temperature, the pot contents solidified. The solids were removed and added to 130 g of an ice/water mixture and combined with 40 mL of water used to wash the pot. This aqueous mixture was stirred for 1 h to dissolve the solids and neutralized with 75 mL of 10N aqueous NaOH. During neutralization, the beaker was cooled with an ice bath. After completing the addition, the mixture was allowed to stand overnight and filtered over a medium frit filter under house vacuum. The collected solids were dried to yield 13.2 g (55%) of the title product.

COMPARATIVE EXAMPLE B

The following method and results were taken from Banks et at., *J. Am. Chem. Soc.*, 73, 3012, (1951) and reiterated here verbatim.

2,4-Diamino-6-hydroxypyrimidine (0.2 mole) was refluxed with 150 mL of phosphorus oxychloride and 1 mL of dimethylaniline for eight hours. The pyrimidine dissolved slowly. The excess phosphorus oxychloride was removed under reduced pressure, leaving a viscous oil which was added to 200 mL of ice and water. After decomposition of the residual oxychloride had occurred, the solution was neutralized with 10N sodium hydroxide with external cooling. The precipitate was filtered off and dried in vacuo at 50° C. The melting point of the crude material was 198°–200° C. The yield was poor. Barbituric acid was converted to 2,4,6-trichloropyrimidine and 2-amino-4,6-dihydroxypyrimidine to 2-amino-4,6-dichloropyrimidine in better than 80% yield by the same procedure.

COMPARATIVE EXAMPLE C

The following method and results were taken from U.S. 3,991,190, Example 1 and reiterated here verbatim.

2-Amino-4,6-dichloropyrimidine was prepared according to a modification of the method of M. J. Langeman, *J. Am. Chem. Soc.*, 73, 3011, (1951 ). To a reaction vessel fitted with a reflux condenser and a heat source there was delivered 2-amino-4,6-dihydroxypyrimidine 1.27 g (0.1 mole), phosphorus oxychloride 13.0 g (0.9 mole) and dimethylaniline 3.6 g (0.3 mole). These ingredients were mixed by swirling and then heated to reflux at about 107° C. for about 8 h.

The excess phosphorus oxychloride was removed by evaporation and the thick, molten residue was poured carefully into 80 mL of hot water (at about 80° C.) with agitation thereby obtaining a suspension. Sufficient concentrated sodium hydroxide solution was added to render the suspension definitely basic, e.g. pH 8–9 or more. The mixture was then filtered and the filter cake was washed with water until the washings were neutral. The product was recrystallized from benzene. There was obtained 2-amino-4,6-dichloropyrimidine having a melting point of 22° C., yield 70%.

COMPARATIVE EXAMPLE D

The following method and results were taken from Kokai Patent No. Sho 64(1989)-83071, Comparative Example 1 and reiterated here verbatim.

One gram of 2-amino-4,6-dihydroxypyrimidine and 9.7 g of phosphorus oxychloride were reacted in accordance with the method recorded in Example 1 of *The Journal of the American Chemical Society* (JACS), 73, page 3012 (1951) to obtain 0.58 g (yield of 45.5% ) of 2-amino-4,6-dichloropyrimidine crystals.

None of the above comparative examples produced a yield of product as great as the present invention. All of the comparative examples used much greater ratios of phosphorous oxychloride and 2-amino-4,6-dihydroxypyrimidine and a higher temperature.

What is claimed:

1. A process for preparing 2-amino-4,6-dichloropyrimidine in the absence of a solvent or in the absence of a large excess of reactant comprising reacting 2-amino-4,6-dihydroxypyrimidine and phosphorus oxychloride at a temperature from 40° C. to 0° C. in the presence of an amine base selected from the group consisting of N-N-dimethylaniline; N,N-diethylaniline, triethylamine, pyridine and picoline, the mole ratio of amine base to 2-amino-4,6-dihydroxypyrimidine being 1.7:1 to 2.5:1, the mole ratio of phosphorus oxychloride to 2-amino-4,6-dihydroxypyrimidine being 2.8:1 to 5:1.

2. The process of claim 1 wherein the temperature is 55°–68° C.

3. The process of claim 1 wherein the mole ratio of phosphorus oxychloride to 2-amino-4,6-dihydroxypyrimidine is 3.4:1 to 4.2:1.

4. The process of claim 1 where the amine base is N,N-dimethylaniline.

5. The process of claim 1 where the amine base is triethylamine.

* * * * *